(12) United States Patent
Filar

(10) Patent No.: US 7,883,210 B2
(45) Date of Patent: Feb. 8, 2011

(54) APPARATUS FOR PHOTOGRAPHING THE ANTERIOR SEGMENT AND RETINA OF THE EYE THROUGH THE USE OF A CAMERA ATTACHMENT

(76) Inventor: Paul A. Filar, 429 N. 7th Ave., Sturgeon Bay, WI (US) 54235

( * ) Notice: Subject to any disclaimer, the term of this patent is extended or adjusted under 35 U.S.C. 154(b) by 151 days.

(21) Appl. No.: 12/386,912

(22) Filed: Apr. 24, 2009

(65) Prior Publication Data

US 2010/0271593 A1 Oct. 28, 2010

(51) Int. Cl.
*A61B 3/14* (2006.01)
*G03B 29/00* (2006.01)
(52) U.S. Cl. .................................... 351/206; 396/18
(58) Field of Classification Search ............... 351/206; 396/18
See application file for complete search history.

(56) References Cited

U.S. PATENT DOCUMENTS

| 6,149,273 | A  | * | 11/2000 | Matthews | ............... 351/221 |
| 6,393,431 | B1 | * | 5/2002 | Salvati et al. | ..................... 1/1 |
| 2005/0110949 | A1 | * | 5/2005 | Goldfain et al. | ............ 351/206 |

* cited by examiner

*Primary Examiner*—Jordan M. Schwartz
(74) *Attorney, Agent, or Firm*—Absolute Technology Law Group, LLC

(57) ABSTRACT

Apparatus for photographing the anterior segment and retina of the eye through the use of a camera attachment designed to snap-fit onto an ophthalmoscope without permanently altering the ophthalmoscope itself. The plastic attachment houses a digital camera with video and still photo capabilities. A button on the camera allows for snapshots to be taken. The camera is connected to a laptop or stationary computer via a USB cable. The camera, which utilizes software for photo and video management, relays views to a computer and monitor, projecting the same view on the screen as a practitioner would see when using the ophthalmoscope traditionally.

1 Claim, 2 Drawing Sheets

APPARATUS FOR PHOTOGRAPHING THE ANTERIOR SEGMENT AND RETINA OF THE EYE THROUGH THE USE OF A CAMERA ATTACHMENT

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of Optometry and Ophthalmology (human and animal) and more specifically, it is an apparatus for photographing the anterior segment and retina of the eye through the use of a camera attachment designed to fit onto a ophthalmoscope, specifically a WELCH ALLYN PANOPTIC ophthalmoscope.

As a Doctor of Optometry I have utilized several ophthalmoscopes and slitlamps and have acquired wonderful views of the eye both anterior segments and retina. When a disease or abnormality is found, it is important to photodocument the view. This is used for photodocumentation and comparison purposes, and also for patient education.

Occasionally, this photodocumentation is utilized in diagnosis by consultations with colleagues. Historically, if a disease or abnormality is found, we must turn to a different piece of equipment to take these photos. This is impossible to do in an out of office setting such as a nursing home, where doctors are unable to transport this bulky and expensive equipment. I felt there was a need to have an easy to use, portable, direct ophthalmoscope camera that I could quickly take photos with and share with patients, print, and save. The WELCH ALLYN PANOPTIC ophthalmoscope offers improved field of view over any other direct ophthalmoscope on the market and is easy to use. I decided to create an attachment that could easily connect and detach from this instrument, without permanently altering its traditional use.

Several retinal cameras exist, including: the CANON NM45 with POLAROID film which evolved into digital, becoming more mainstream with technological advancements in cameras; a few bulky portable cameras, such as NIDEK, Macular Blue, and FLEXISCOPE are also on the market. The following patent list identifies a few ideas with similar goals of accurate photodocumentation, but different means of obtaining that goal:

U.S. Pat. No. 4,304,483 Dec. 8, 1981 Whitten

U.S. Pat. No. 6,729,727 May 4, 2004 Nanjo

U.S. Pat. No. 7,364,297 Apr. 29, 2008 Goldfain, et al.

U.S. Pat. No. 5,713,047 Jan. 27, 1998 Kohayakawa

U.S. Pat. No. 7,448,753 Nov. 11, 2008 Chinnock

Inadequacies in the prior technology related to this patent include: being too large, bulky, and expensive; lack of an anterior and retinal camera combinations; limited field of view through ophthalmoscopes of approximately five degrees; cameras which require a flash; beam splitters mounted on the instruments to separate the optics; being clumsy to use; taking photographs of poor quality; and permanently altering existing equipment.

My invention provides the following differences and advantages over prior technology: physically small and efficient; relatively inexpensive; portable (can be used with any laptop or stationary computer); an improved 25 degree field of view; utilizes standard examination illumination; uses a direct view (no beam splitter); user-friendly; the camera takes photos and video of the anterior segment AND retina of the eye with one instrument, without any complicated adjustments or alterations; easily photographs or record videos of the retina through dilated or non-mydriatic pupils; and utilizes a higher resolution digital camera.

BRIEF SUMMARY OF THE INVENTION

The primary object of the invention is to provide a user-friendly anterior segment and retinal camera that is physically small and makes efficient use of time and current technology.

Another object of the invention is to take photos and video of the anterior segment AND retina of the eye with one instrument, without any complicated adjustments or alterations.

Another object of the invention is for it to be used in conjunction with the WELCH ALLYN PANOPTIC ophthalmoscope for photodocumentation or video of any eye, human or animal.

A further object of the invention is to take advantage of proven WELCH ALLYN optics—camera attaches only to the WELCH ALLYN PANOPTIC ophthalmoscope.

Yet another object of the invention is to provide portable technology (it can be used anywhere with a laptop or stationary computer).

Still yet another object of the invention is to utilize digital photography, video, and computer software for patient ocular care and quality medical records.

Another object of the invention is to take photos that have time and date stamps.

Another object of the invention is to photograph or record video of the retina through dilated or non-mydriatic pupils.

A further object of the invention is to photograph or record video of the anterior segment of the eye.

Yet another object of the invention is to house a camera in a secure position on the ophthalmoscope.

Still yet another object of the invention is to allow the camera housing to be easily attached and detached, without permanently altering existing equipment (e.g., WELCH ALLYN PANOPTIC ophthalmoscope).

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed an apparatus for photographing the anterior segment and retina of the eye through the use of a camera attachment designed, to snap-fit (FIG. 2 and reference point 26) onto a WELCH ALLYN PANOPTIC ophthalmoscope comprising: a plastic attachment that houses a digital camera (FIG. 1), a plastic fin grip to allow easy removal (reference point 21), side plates to prevent semi-tubular apparatus from rotating (reference point 25), a digital camera with video and still photo capabilities (reference point 24), a button on the camera allowing for snapshots to be taken (reference point 22), a USB connection from the camera to a computer (reference point 23), software for photo and video management, and a relayed view to a computer and monitor that projects the same view a practitioner would see when using the WELCH ALLYN PANOPTIC ophthalmoscope traditionally.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
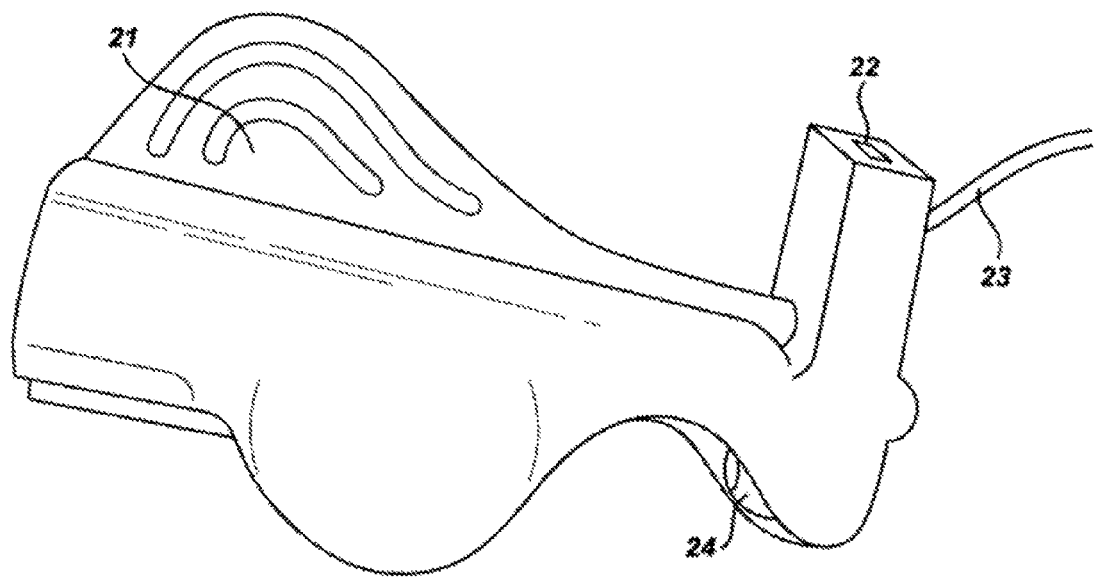
FIG. 1 is a side perspective view of the invention. The semi-tubular apparatus follows the contours of the WELCH ALLYN PANOPTIC ophthalmoscope and houses the digital camera.
Figure 2:
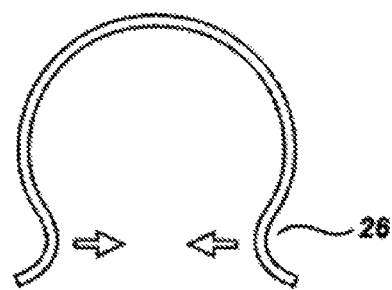
FIG. 2 is a front view of the apparatus's snap-fit design to grip the WELCH ALLYN PANOPTIC ophthalmoscope barrel.
Figure 3:
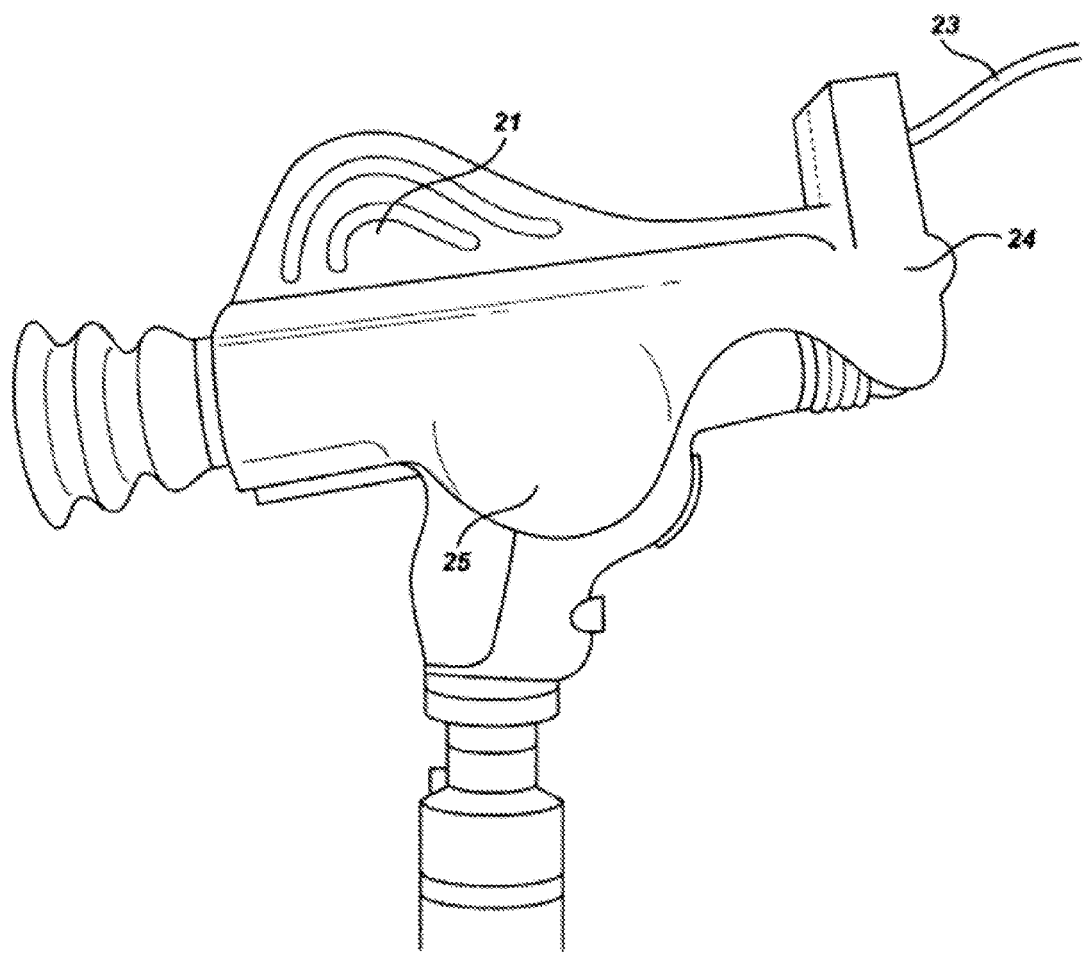
FIG. 3 is a side perspective view of the invention as mounted onto the WELCH ALLYN PANOPTIC ophthalmoscope.

The present invention is a plastic apparatus that houses a digital camera and attaches to the WELCH ALLYN PANOPTIC ophthalmoscope. The camera could be secured to the WELCH ALLYN PANOPTIC ophthalmoscope in many ways, but this housing, designed with its snap fit (reference point 26) and side plates (reference point 25), has proven most stable. The apparatus is comprised of a camera (reference point 24) that fits snuggly against the practitioner's brow rest and a plastic housing that snaps down onto the ophthalmoscope from the top of the instrument. The shape and material of the plastic allows the snap action (see FIG. 2). The tight fit of the plastic housing on the top front of the ophthalmoscope (FIG. 2) provides forward tension which keeps the camera in proper position (reference point 24 in FIG. 3). This arrangement, along with the plastic fin grip (reference point 21) also allows the plastic camera housing/attachment to be quickly and easily attached and detached, while still providing a stable camera position on the WELCH ALLYN PANOPTIC ophthalmoscope. The design of the camera and the plastic housing allows the setup to have a snapshot button (reference point 22) directly on the camera to take the photo. This keeps the user's hands on the instrument for further stability and alignment while photographing the desired pathology or structure. Once the camera is in place, the user can utilize the existing WELCH ALLYN PANOPTIC ophthalmoscope's optics to easily photograph or video the anterior segment or retina of the eye. The camera is connected to a laptop or stationary computer via a USB cable (reference point 23). The software installed on the computer allows for further customization and management of the camera features, including but not limited to: megapixel size, zoom, alignment, time and date stamping, video capabilities, and focusing. The image relayed on the computer monitor projects the same view a practitioner would see when traditionally using the WELCH ALLYN PANOPTIC ophthalmoscope. Through the use of this apparatus, practitioners can maintain accurate patient photodocumentation records.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. Apparatus for photographing the anterior segment and retina of an eye comprising:
    an integrally constructed plastic attachment;
    a digital camera substantially and not entirely housed in a first portion of said integrally constructed plastic attachment, said digital camera having video and still photo capabilities;
    an ophthalmoscope substantially and not entirely housed in a second portion of said integrally constructed plastic attachment, said ophthalmoscope in optical communication with said digital camera;
    wherein said digital camera and said ophthalmoscope photograph the anterior segment and the retina of an eye;
    a means for securing said digital camera to said ophthalmoscope wherein said digital camera and said ophthalmoscope are held in optical communication with each other by said integrally constructed plastic attachment and said means for securing;
    a means for taking snapshots;
    a means for connecting said digital camera to a computer;
    wherein said digital camera relays views to a computer and monitor, projecting the same view a practitioner would see when using said ophthalmoscope without the use of said digital camera.

* * * * *